United States Patent

Moubayed et al.

[11] Patent Number: 5,924,852
[45] Date of Patent: Jul. 20, 1999

[54] LINEAR PERISTALTIC PUMP

[76] Inventors: Ahmad-Maher Moubayed, 22212 Destello, Mission Viejo, Calif. 92691; Rogelio Blanco Jester, Lago Tanganica 716, Jardines Del Lago, Mexicali, B.C., Mexico

[21] Appl. No.: 08/751,548

[22] Filed: Nov. 18, 1996

Related U.S. Application Data

[63] Continuation-in-part of application No. 08/615,704, Mar. 12, 1996, Pat. No. 5,575,631.

[51] Int. Cl.[6] ................................................ F04B 43/08
[52] U.S. Cl. .................................... 417/474; 604/153
[58] Field of Search ................................ 417/474, 478, 417/479, 480; 604/153; 92/62

[56] References Cited

U.S. PATENT DOCUMENTS

| | | | |
|---|---|---|---|
| 2,393,838 | 1/1946 | Tarbox | 417/474 |
| 3,127,845 | 4/1964 | Voelcker | 417/478 |
| 3,518,033 | 6/1970 | Anderson | 417/197 |
| 5,092,749 | 3/1992 | Meijer | 417/474 |

Primary Examiner—Timothy Thorpe
Assistant Examiner—Peter G. Korytnyk
Attorney, Agent, or Firm—John R. Duncan; Frank D. Gilliam

[57] ABSTRACT

A peristaltic pump for pumping liquids through a resilient tube. In one embodiment, the pump includes a curved concave platen against which a resilient tube is placed. A multi lobed cam is positioned adjacent to the platen and tube. A plurality of pump fingers are mounted between tube and cam in a manner permitting radial movement of the pump fingers. As the cam rotates, the fingers are pressed toward the tube sequentially so as to pump liquid through the tube. The lobe end should press the tube sufficiently to occlude the tube and prevent back flow without over pressing and damaging the tube. A transverse pinch finger is provided on each pump finger, extending from the tube pressing face of each pump finger. At the tube occluding position, the pump finger nearly occludes the tube and the pinch finger completes occlusion without pressing the tube beyond the fully occluded position. A fixed or slidable spring pressed pinch finger may be used. In a second embodiment, the pump fingers also include pinch fingers and are moved toward and away from a planar platen by a plurality of cams mounted transversely on a rotatable shaft. The pinch fingers operate in the same manner as in the first embodiment.

8 Claims, 3 Drawing Sheets

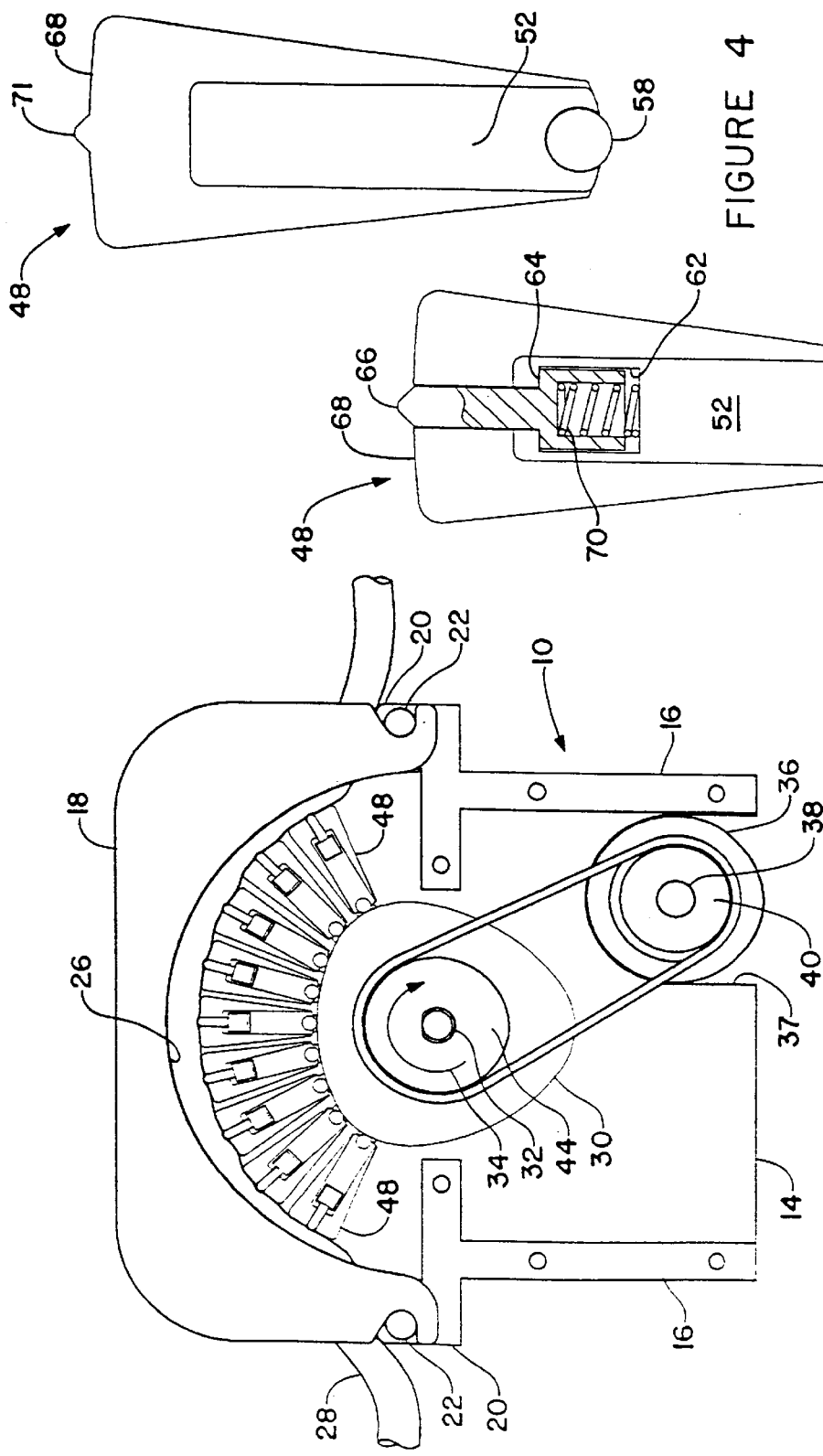

LINEAR PERISTALTIC PUMP

This application is a Continuation-in-Part of Ser. No. 08/615,704, filed Mar. 12, 1996, now U.S. Pat. No. 5,575,631, issued Nov. 19, 1996.

BACKGROUND OF THE INVENTION

This invention relates in general to fluid pumps and more specifically to a peristaltic pump having cam driven plurality of fingers for sequentially engaging a resilient tube to create liquid flow through the tube.

Conventional linear and rotary peristaltic pumps typically have a section of resilient tubing positioned between a wall and a set of rollers or reciprocating pushers that progressively compress sections of the tubing to pump liquids. Such pumps are often used in medical applications, such as intravenous infusion or withdrawing fluids such as in a wound drainage system. These pumps operate in a positive manner and are capable of generating substantial outlet pressures.

Typical linear peristaltic pumps include those described by Sorg et al. in U.S. Pat. No. 2,877,714, Borsannyi in U.S. Pat. No. 4,671,792 Heminway et al. in U.S. Pat. No. 4,893,991 and Canon in U.S. Pat. No. 4.728,265. While generally effective, these pumps are large, complex and cumbersome, requiring a drive shaft parallel to a resilient tube and a plurality of cams along the drive shaft to move pushers toward and away from the tube.

Rotary peristaltic pumps generally dispose a resilient tube along a circular path, with a number of rollers mounted around the circumference of a circular rotor sequentially rolling along the tube to occlude the tube and force liquid through the tube. Typical of such pumps are those disclosed by Soderquist et al. in U.S. Pat. No. 4,886,431 and Kling in U.S. Pat. No. 3,172,367. These pumps often have relatively low efficiency and impose high shear and tension stresses on the tube causing internal tube wall erosion or spallation. The tube may eventually be permanently deformed so that the tube becomes flattened into a more oval shape and carries less liquid.

Another type of peristaltic pump has a tube arranged along a circular path with a cam member within the circle sequentially moving a plurality of blunt pushers or fingers outwardly to sequentially compress the tube from one end of the path to the other. Typical of these pumps are those shown by Gonner in German Patent No. 2,152,352 and Tubospir in Italian Patent No. 582,797.

These pumps tend to be less complex than linear peristaltic pumps. However, the pressure imposed by the blunt fingers reduces tube life, sometimes causing internal tube wall erosion or spallation, which results in particulate matter getting into the fluid stream. Tubes with different wall thicknesses cannot be accommodated by these pumps, since with thinner than standard tubes the fingers will not properly occlude the tube and with thicker than standard tubes the tube will close prematurely and be subject to excessive compression, requiring higher cam drive power and causing excessive wear on the cam and tube.

Thus, there is a continuing need for peristaltic pumps of greater simplicity, small size, low drive power requirements and which can accommodate resilient tubes of varying wall thickness while reducing wear and internal erosion of the resilient tube.

SUMMARY OF THE INVENTION

The above-noted problems, and others, are overcome in accordance with this invention by a peristaltic pump having, in one embodiment, a concave curved, generally circular, platen for supporting a resilient tube, a multi-lobe cam rotatable about the center of the platen concavity, and a plurality of pump fingers riding on the cam as cam followers and guided to move in a radial direction toward and away from said platen.

In another embodiment, the pump has a generally planar platen for supporting a resilient tube, a plurality of parallel cams mounted on a rotatable shaft, a plurality of pump fingers, each riding on one of said cams.

Each pump finger has a face for engaging a tube on said circular or planar platen. Each face includes a narrow pinch finger spring centered in the face and biased to extend beyond the face.

Upon rotation of the cam or cams, the pump finger closest to the highest area on the corresponding cam in the direction of rotation will be moved outwardly in a radial direction to squeeze the tube against the platen. As the cam or cam assembly continues to rotate, the second pump finger will squeeze the tube as the pinch finger on the first pump finger occludes the tube, to force liquid in the tube to flow in the desired direction as the cam or cam assembly rotates. As cam rotation continues, the subsequent fingers will sequentially squeeze the tube to push liquid and then occlude the tube. At the same time, a pump finger just behind a lobe will move away from the tube, allowing the tube to expand and fill with liquid. This sequence continues as cam rotation proceeds.

BRIEF DESCRIPTION OF THE DRAWING

Details of the invention, and of preferred embodiments thereof, will be further understood upon reference to the drawing, wherein:

FIG. 2 is a side elevation of the pump of FIG. 1 at the beginning of a pumping cycle with the casing closed and the near side casing removed to show the internal components;

FIG. 3 is a detail side elevation view of the first pump embodiment pump finger assembly having a spring biased pinch finger and with the pinch finger partially cut-away;

FIG. 4 is a detail side elevation view of a pump finger for use with the first pump embodiment with an alternate pinch finger embodiment;

DETAILED DESCRIPTION OF PREFERRED EMBODIMENTS

Figure 1:
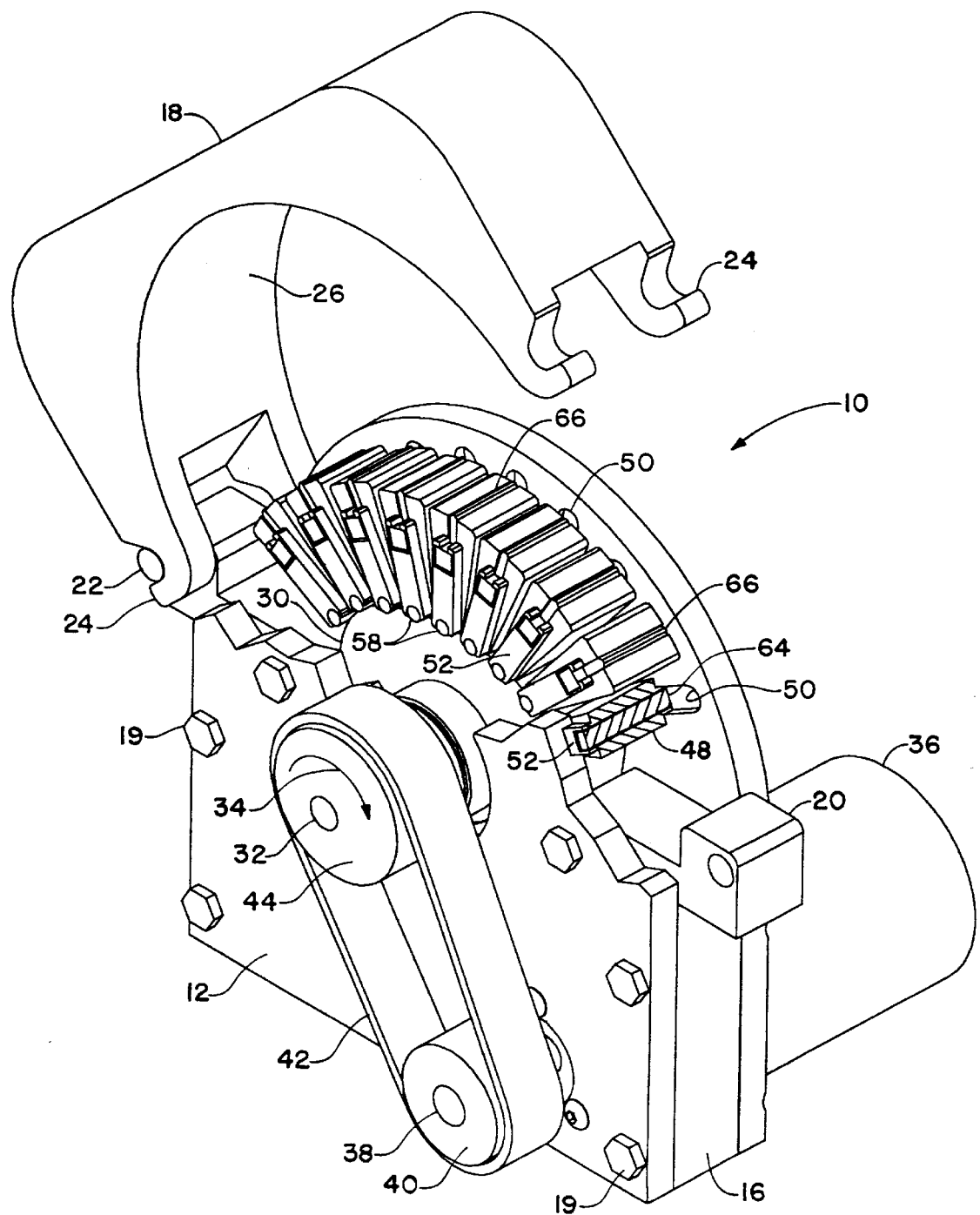
FIG. 1 is a perspective view of a first embodiment of our pump with the casing open and partially cut-away and one pump finger and pinch finger cut-away.

Referring to FIGS. 1 and 2, there is seen a curvilinear peristaltic pump 10 having a casing basically consisting of a front plate 12, a back plate 14 and spacers 16. The casing is held together by a plurality of bolts 19 for ease of assembly and disassembly as needed. A removable cover 18 is secured to casing 10. Each spacer 16 includes a block 20 having a hole therethrough cooperating with a pin or bolt 22 and hook-shaped cover extensions 24 to hold cover in place.

Cover 18 includes a concave curvilinear platen 26. While platen 26 may have any suitable surface, generally a cylindrical surface is preferred. As best seen in FIGS. 2 and 3, a resilient tube 28 may be laid along platen 26, exiting through the open space between each pair of extensions 24.

A multi-lobed cam 30 is mounted for rotation about an axle 32 that extends through suitable bearings in front and back plates 12 and 14. Cam 30 may have any suitable number of lobes, two or more. For optimum performance with smallest size, the three-lobe cam shown is preferred. Where platen 26 is cylindrical, axle 32 is preferably at the axis of the platen. Cam 30 can be rotated in either direction to pump liquid through tube 28 in either direction. For convenience of operation explanation, cam 30 will be considered to be rotating clockwise, as indicated by arrow 34. Any suitable drive means may be used to rotate cam 30. In the preferred embodiment shown, an electric drive motor 36 extends through opening 37 in back plate 14 and is mounted on the back surface of front plate 12. Motor 36 has a drive shaft 38 extending through front plate 12 to a pulley 40. A drive belt 42 extends from pulley 40 to pulley 44 mounted on cam axle 32. Pulleys 40 and 44 are sized to provide the desired cam rotation speed. A variable speed motor 36 may be used to allow cam rotation speed to be easily varied. If desired, a gear system could be used in place of belt 42, or a different drive system could be used, such as a conventional hydraulic drive, in place of the electric motor and belt drive system shown.

A plurality of pump fingers 48, as best seen in FIGS. 1 and 3, are mounted for radial movement on front plate 12 and back plate 14 between cam 30 and platen 26. Any suitable number of pump fingers 48 may be used. Where a greater number of cam lobes are used, fewer fingers will generally be used. On the other hand, if narrow fingers 48 are used, a larger number may be provided. A large scale pump will generally use a larger number of fingers. A preferred number of pump fingers 48 for a three-lobe cam 30 of maximum efficiency coupled with small size is from 7 to 11 pump fingers, with 9 generally being optimum. As seen in FIG. 1, a plurality of opposed radial grooves 50 are provided in front plate 12 and back plate 14 to receive side extensions 52 that extend into grooves 50 and are freely movable therealong.

Each pump finger 48, as best seen in FIG. 3, includes a cylindrical recess 54 at a first end 56 for rotatably receiving a bearing roller 58. Rollers 58 freely roll on the surface of cam 30 in the manner of roller bearings, reducing wear on the cam surface. Side extensions 52 as seen in FIG. 1 are formed on the sides of pumping finger 48. A transverse, inverted "T" slot 62 is formed across the top of pump finger 48. A base 64 mounting a transverse pinch finger 66 fits within slot 62, with pinch finger 66 extending through a transverse slot in the pumping surface along second end 68 of pump finger 48, as seen in FIG. 1. A spring 70 biases base 64 and pinch finger 66 toward the extended position.

The pump operates in the following manner. As seen in FIG. 2, two lobes of cam 30 are located at the beginning and end of the series of pump fingers 48. At this position, pump fingers 48 engaging the central portion of tube 28 along the middle of platen 26 are relatively withdrawn and those at the ends are relatively extended, thereby creating a zone of occlusion. Thus, the central portion of tube 28 is filled with liquid and the ends are substantially occluded. As cam 30 rotates in the direction of arrow 34, the second left pump finger 48 is pressed further against tube 28 while the rightmost pump finger begins to withdraw. Liquid is thus pushed in a zone of occlusion toward the right or outlet end of tube 28 and begins to exit. As cam rotation continues, pump fingers 48 are sequentially extended from the left and withdrawn at the right, forcing liquid in tube 28 toward the outlet end.

As seen in the central region of tube 28 in FIG. 2, pinch fingers 66 under the forces of springs 70 are relatively extended. The leftmost pump finger 48 is slightly extended, but second end 68 of pump finger 48 has not entirely occluded tube 28. Pinch finger 66 is extended sufficiently under the force of spring 70 to occlude the tube. With a thin wall tube 28, pinch finger 66 will extend further to close the tube with a thick walled tube, pinch finger will only extend a shorter distance until the tube is closed. Thus, only enough force is applied through the pinch finger to close the tube.

In prior art pumps, the pumping finger extended only a single preset distance under the strong mechanical force of a cam. With those arrangements, thin tubes are not entirely occluded and thick walled tubes are crushed beyond closure, often resulting in rapid wear, internal wall erosion and spallation with the resulting injection of particles of wall material into the liquid stream, of great concern in many infusion operations. Only a short degree of extension and retraction of pinch fingers 66 is required to produce this highly advantageous result, typically from about 0.2 to 1.0 mm.

FIG. 4 shows a side elevation view of a second embodiment of pump fingers 48. Here the pump fingers 48 use a pinch finger in the form of a fixed transverse ridge 71 across the surface 68 of the pump fingers in place of the spring biased pinch fingers 66 of the embodiment of FIG. 3. While the FIG. 3 embodiment is generally preferred for lowest tube wear and the ability to work well tubes of slightly varying diameter and wall thickness, in other cases the lower cost version of FIG. 4 may be preferred where the tube is more dimensionally uniform or the motor has sufficient power and the tube can take greater compression.

Figure 5:
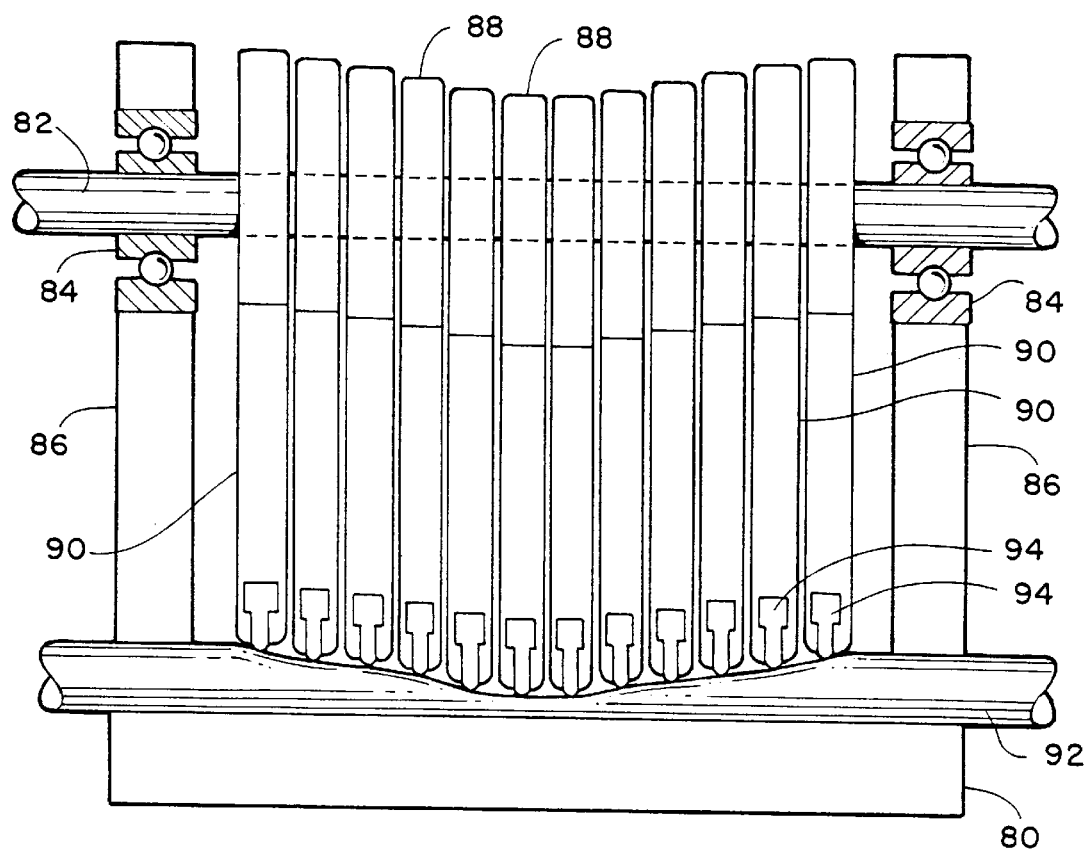
FIG. 5 is an elevation view, partially cut away, of a second embodiment of out pump, having a planar platen.
Figures 6, 7:
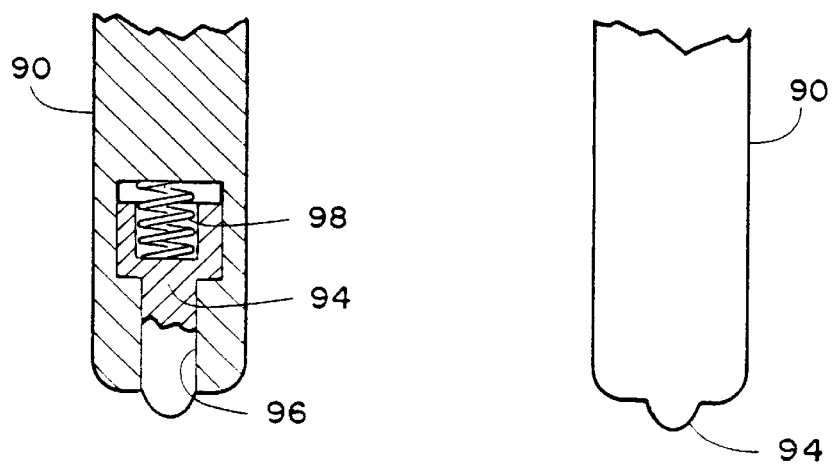
FIG. 6 is a detail view, partially cut away, of one embodiment of a pinch finger useful with the pump of FIG. 5.
FIG. 7 is a detail view of a second embodiment of a pinch finger useful with the pump of FIG. 5.

FIGS. 5–7 schematically illustrate a second embodiment of out peristaltic pump, having a linear platen 80. A shaft 82 is rotatably mounted through bearings 84 on posts 86 with the shaft generally parallel to platen 80.

A plurality of cams 88 are fixed to shaft 82 in a contiguous, parallel relationship. Cams 88 may have any suitable configuration. Typically, cams 88 could have a circular periphery with the shaft passing through each cam off center, could be an ellipse, could be multi-lobed as cam 30 in FIG. 2, etc. The line passing through shaft 82 and the outermost portion of each cam is progressively radially offset through the set of cams.

Each cam 88 engages a pump finger 90 for longitudinal movement with the change in diameter of the corresponding cam. Each pump finger 90 may slide between front and back walls (not shown for clarity of illustration) of the sort shown in FIG. 1 or any other suitable guide means. As each cam rotates, the corresponding pump finger 90 moves upwardly and downwardly in accordance with the cam surface. When a tube 92 is placed on platen 80, the pump fingers 90 will sequentially press against the tube to occlude the tube and progressively pump liquid through he tube in the manner described above.

As explained above, since tube wall thickness will vary, pressing a blunt pump finger 90 against a tube is likely to damage some tubes. To overcome this, a pinch finger 94 is used to fully occlude only a central area along each pump finger 90. Two embodiments of a suitable pinch finger are shown in detail view of FIGS. 6 and 7.

In the optimum embodiment of FIG. 6, pinch finger 94 is slidably mounted in a "T" shaped slot 96 within an end of each pump finger 90. Pinch finger 94 has a corresponding shape and is movable a predetermined distance toward and away from the platen. A spring 98 presses pinch finger 94 toward platen 80. Thus, as a cam 88 moves the corresponding pump finger 90 toward tube 92, the tip of pinch finger 94 begins to occlude the tube. Once tube 92 is fully occluded, with the opposite tube walls in contact, pinch finger 94 is pushed back into pump finger 90 against spring 98 to prevent the tip from being forced into the tube to the extent that the tube is damaged.

An alternate embodiment of pinch finger 94 is illustrated in the detail view of FIG. 7. In this embodiment, pinch finger 94 is in the form of a ridge across the end of pump finger. As this pump finger is moved toward a tube 92 by the corresponding cam 88, pinch finger occludes the tube along a transverse line. While minor damage may occur if pinch finger 94 is pressed too far into tube 92, the damage will be less than if an entire blunt pump finger end was similarly overly pressed against the tube. Where tubes have consistent wall thicknesses, this embodiment provides excellent results. With tubes of varying wall thickness, the embodiment of FIG. 6 is optimum.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

We claim:

1. A linear peristaltic pump which comprises:

a generally planar platen;

a rotatable cam assembly spaced from said platen;

said cam assembly comprising a plurality of contiguous cams mounted on a shaft with lobes of said cams sequentially radially offset along said shaft;

means for rotating said shaft and cam assembly in a first direction;

a plurality of substantially parallel pump fingers, each having a first end riding on one of said cams and a second end adjacent to said platen;

said cam assembly configured to first sequentially move said pump fingers toward said platen and second a sequentially allow said pump fingers to move away from said platen;

each of said pump fingers having a pinch finger extending beyond said second end, transversely across said second end;

whereby a resilient tube may be interposed between said platen and said second pump finger ends so that as said pump fingers are sequentially moved toward said platen, liquid in said tube is pumped in said first cam rotation direction and each pinch finger will occlude said tube when each said pump finger reaches a position closest to said platen.

2. The linear peristaltic pump according to claim 1 wherein each said pinch finger comprises a slidable member extending through a transverse slot in each pump finger second end and further including means for biasing each said pinch finger in a direction extending outwardly of said transverse slot.

3. The linear peristaltic pump according to claim 1 wherein each said pinch finger is a transverse ridge across each said pump finger second end.

4. The linear peristaltic pump according to claim 1 wherein each of said pump fingers has a transverse cavity communicating with said transverse slot, a base member within said cavity supporting a pinch finger in said transverse slot, with a compression spring between said base member and a wall of said cavity opposite said pinch finger.

5. A linear peristaltic pump which comprises:

a substantially planar platen;

a rotatable cam assembly spaced from said platen;

said cam assembly comprising a plurality of cams transversely mounted on a shaft;

means for rotating said cam assembly in a first direction;

a plurality of pump fingers, each having a first end riding on one of said cams and a second end adjacent to said platen;

a resilient tube interposed between said platen and said pump fingers;

said cams configured to first sequentially move said pump fingers toward said platen to compress said tube and second, a sequentially allow said pump fingers to be moved away from said platen by tube resiliency as said cam assembly is rotated on said shaft;

each of said pump fingers sized to compress said tube as said cams move said pump fingers toward said platen but to not fully occlude said tube; and each of said pump fingers having a pinch finger extending transversely beyond said pump finger second end to fully occlude said tube as said cams move said pump fingers fully toward said platen.

6. The linear peristaltic pump according to claim 5 wherein each said pinch finger comprises a slidable member extending through a transverse slot in each pump finger second end and further including means for biasing each said pinch finger in a direction extending outwardly of said transverse slot.

7. The linear peristaltic pump according to claim 5 wherein each said pinch finger is a transverse ridge on each said pump finger second end.

8. The linear peristaltic pump according to claim 5 wherein each of said pump fingers comprises an elongated body having a transverse slot across said second end, extending into said pump finger and communicating with a cavity, said pinch finger slidably fitting within said slot and secured to a base in said cavity and further including a compression spring between said base and a wall of said cavity opposite said pinch finger to bias said pinch finger outwardly of said transverse slot.

* * * * *